US00PP08459P

United States Patent [19]

Veenstra

[11] Patent Number: Plant 8,459

[45] Date of Patent: Nov. 9, 1993

[54] DAHLIA PLANT NAMED WENDY

[75] Inventor: H. Veenstra, BM Enkhuizen, Netherlands

[73] Assignee: Royal Sluis Inc., Salinas, Calif.

[21] Appl. No.: 923,812

[22] Filed: Aug. 3, 1992

[51] Int. Cl.[5] ..... A01H 5/00

[52] U.S. Cl. ..... Plt./87.8

[58] Field of Search ..... Plt./87.8

[56] References Cited

PUBLICATIONS

Boyer et al. 1989. *American Dahlia Society Composite Classification of Dahlias*, 1976–1989. p. 76.

*Primary Examiner*—James R. Feyrer
*Assistant Examiner*—Elizabeth C. Kemmerer
*Attorney, Agent, or Firm*—Christie, Parker & Hale

[57] ABSTRACT

A variety of Dahlia with low plant growing habit producing attractive pink flowers is described.

1 Drawing Sheet

BACKGROUND OF THE INVENTION

The present invention relates to a new and distinct variety of dahlia plant known by the varietal denomination 'Rowendy'.

'Rowendy' is a product of a breeding and selection program in which the female and male parents were selected proprietary seedlings of my creation identified by numbers 881600 and 881602, respectively. The parents were descendants from the variety 'Figaro', a well known seed dahlia, which is regarded as a standard for flower form habit and leaf size, but having little or no similarity to the new variety. The new variety was asexually reproduced.

SUMMARY OF THE INVENTION

The new variety is an attractive dahlia plant with low growing habit which produces attractive pink flowers against a background of attractive, abundant medium green foliage. The plant is compact and suitable to both pot plant production and for use in outdoor gardens. Inflorescence is compact and extends above foliage with flowers borne on relatively short pedicels. Plant height at flowering is about 18 cm.

Asexual reproduction by cuttings of the new variety at Parrish, Fla. has demonstrated that the combination of characteristics as described herein for 'Wendy' are firmly fixed and are retained through successive generations of asexual reproduction. Cuttings of the new variety produce a good branching root system, which, on the adult plant, are compact finger-shaped tubers that develop a number of young buds at the tuber crown which grow out in the early spring period.

'Rowendy' has not been observed under all possible environmental conditions. The phenotype may vary with variations in environment such as temperature, light intensity, day length and cultural conditions.

BRIEF DESCRIPTION OF THE DRAWINGS

The accompanying color photographic illustration shows a typical specimen of the new variety in colors as nearly true as possible with an illustration of this type. The illustration depicts growth habit, flower position relative to leaves and flower color.

DETAILED DESCRIPTION OF THE NEW VARIETY

In the following description, color references are to The Royal Horticultural Society Colour Chart, where color values refer to color plate numbers in this chart.

The closest variety to 'Rowendy' is the variety 'Betty', U.S. Plant Pat. No. 7,762. The new variety differs from 'Betty' in flower coloration and plant habit, as well as flower size.

The following observations are of plants described and grown in Enkhuizen, The Netherlands under greenhouse and outdoor conditions which approximate those generally used in commercial practice. Among the traits possessed by the new variety which in combination distinguish it from other varieties are its compact plant habit of growth, light pink flower color and flower size.

Species: Dahlia.
Botanical name: Dahlia Cav.
UPOV Group: Group V — decorative — Class D.
Breeder's reference: 914826/Rowendy.

The new variety is a seedling.

Parentage:
- *Female parent.*—Seedling No. 881600.
- *Male parent.*—Seedling No. 881602.

Plant:
- *Height at flowering.*—About 18 cm.
- *Growth habit.*—Compact; height at flowering central bud stage about 15 cm and at full flowering stage about 18 cm; compact with short internodes and direct basic branching.

Foliage at maturity:
- *Density.*—Abundant.
- *Size.*—Small; length about 6 cm; width about 3 cm, leaves relatively narrow and generally ovate with acute tip.
- *Shape.*—Narrow — serrated.
- *Color.*—Medium Green near 137B.
- *Texture.*—Dull.

New growth:
- *Color.*—New stem — light red/green.
- *Plant habit.*—Rounded.

Stem*:
- *Internode length.*—Very short, about 25 mm.

*Strength.*—Medium to strong.

*Anthocyanin coloration.*—Present.

*Intensity of anthocyanin coloration.*—Strong.

*Distribution of anthocyanin.*—Uniform, in the upper half of the plant.

*Hairs at nodes.*—Present, sparse.

Leaf*:

*Length.*—Very short, about 100 mm.

*Width.*—Very narrow, about 55 mm.

*Color.*—Medium green.

*Glossiness.*—Weak.

Peduncle*:

*Length.*—Very short, about 60 mm.

Flowering:

*Habit.*—Nearly continuous.

*Color of flowering stem.*—Red/green.

Flower pedicel:

*Angle at which flower is held.*—About 120°.

*Approx. length of pedicel (from flower to top pail of leaves).*—About 3 cm.

*Flower diameter.*—About 9 cm.

Inflorescence: Compact, above foliage.

Flowers:

*Florets.*—Firm, short narrow, blunt, flat.

*Color.*—Light pink with central circular display of yellow reproductive organs.

*Flowering.*—The flower grows above the foliage, the length of the pedicel is about 6 cm (from flower to top pair of leaves); The flower angle in relation to the flower stem is about 120 degrees at the start of flowering and about 90 degrees at full flowering stage; The flower is fertile and can product a small amount of seeds. It is not necessary to pinch the plant for continuous flowering; information supplied is from nonpinched plants.

*Flower head*.*—Angle relative to peduncle: Between 45° and 90°. Type: Semi-double. Diameter: Small, about 82 mm. Height (double heads only): Not applicable. Bracts among ray florets: Clearly visible. Number of ray florets: Medium, about 65.

*Ray floret*.*—Length: Short, about 35 mm. Width: Narrow, about 16 mm. Length/width ratio: Low. Longitudinal axis: Incurved, recurving slightly at the tip. Transverse axis at midpoint: Strongly concave. Lateral margin at middle of floret: Flat. Tip: Pointed. Distribution of pigment: Nonuniform. Type of variation with nonuniform color: Bicolor. Bicolor and variegated varieties only: Distribution of color variation: Zoned. Principal color of inner side: RHS 68B but slightly more intense. Secondary color of inner side: RHS 60B but brighter in the lower third of the floret. Tertiary color of inner side: Not applicable. Principal color of outer side: RHS 74D.

*Color of petals in main florets.*—Half open: Upper surface — near 68B to 68A. Lower surface — Near 65A. Fully open: Upper surface — near 68C to 68B. Lower surface — near 65B. Petal color near center: Near 57A. Central circular display of reproductive organs: Near 23A.

*indicates observations made of plants grown under glass at Cambridge, U.K. by the Plant Variety Testing Office.

I claim:

1. A new and distinct variety of dahlia plant named 'Wendy', substantially as shown and described.

* * * * *

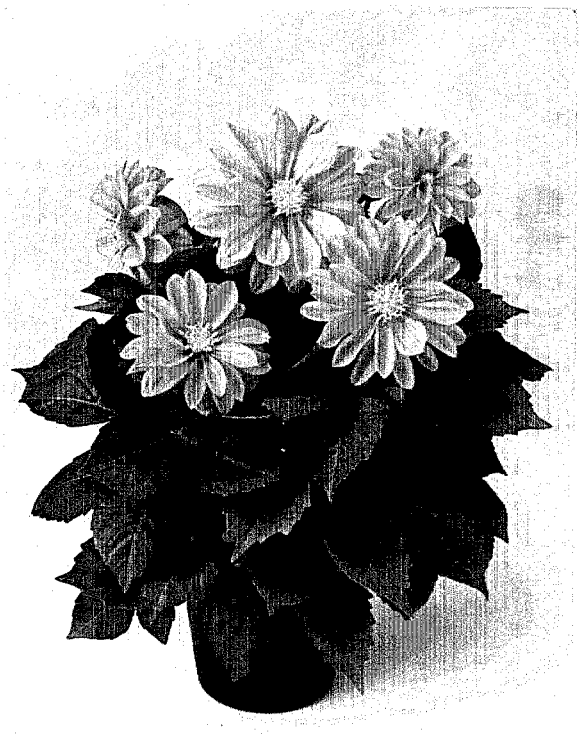

UNITED STATES PATENT AND TRADEMARK OFFICE

CERTIFICATE OF CORRECTION

PATENT NO. : Plant 8,459

DATED : November 9, 1993

INVENTOR(S) : H. Veenstra

It is certified that error appears in the above-indentified patent and that said Letters Patent is hereby corrected as shown below:

On the Title Page:

[54] Title, change "DAHLIA PLANT NAMED WENDY" to -- DAHLIA PLANT NAMED ROWENDY --.

Column 3, line 35, change "product" to -- produce --.

Signed and Sealed this

Eleventh Day of October, 1994

*Attest:*

*Attesting Officer*

Bruce Lehman

BRUCE LEHMAN

*Commissioner of Patents and Trademarks*